United States Patent
Krop et al.

(10) Patent No.: US 12,171,807 B2
(45) Date of Patent: *Dec. 24, 2024

(54) USE OF BREMELANOTIDE IN PATIENTS WITH CONTROLLED HYPERTENSION

(71) Applicant: Cosette Pharmaceuticals, Inc., Bridgewater, NJ (US)

(72) Inventors: Julie Krop, Boston, MA (US); Laura Ann Williams, Sudbury, MA (US)

(73) Assignee: Cosette Pharmaceuticals, Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/158,712

(22) Filed: Jan. 24, 2023

(65) Prior Publication Data
US 2023/0158118 A1 May 25, 2023

Related U.S. Application Data (63) Continuation of application No. 17/154,593, filed on Jan. 21, 2021, now Pat. No. 11,590,209.

(60) Provisional application No. 62/963,719, filed on Jan. 21, 2020.

(51) Int. Cl.
| | |
|---|---|
| A61K 38/12 | (2006.01) |
| A61K 9/00 | (2006.01) |
| A61K 38/34 | (2006.01) |
| A61K 47/10 | (2017.01) |

(52) U.S. Cl.
CPC ............ *A61K 38/34* (2013.01); *A61K 9/0019* (2013.01); *A61K 38/12* (2013.01); *A61K 47/10* (2013.01)

(58) Field of Classification Search
CPC .................................. A61K 38/08; C07K 7/54
See application file for complete search history.

(56) References Cited

U.S. PATENT DOCUMENTS

| | | |
|---|---|---|
| 3,853,836 A | 12/1974 | Greven |
| 3,862,928 A | 1/1975 | De Wied et al. |
| 4,623,715 A | 11/1986 | Geiger et al. |
| 4,649,191 A | 3/1987 | Hruby |
| 5,420,109 A | 5/1995 | Suto et al. |
| 5,569,647 A | 10/1996 | Fauchere et al. |
| 5,576,290 A | 11/1996 | Hadley |
| 5,674,839 A | 10/1997 | Hruby et al. |
| 5,693,608 A | 12/1997 | Bechgaard et al. |
| 5,714,576 A | 2/1998 | Hruby et al. |
| 5,731,408 A | 3/1998 | Hadley et al. |
| 5,908,609 A | 6/1999 | Lee et al. |
| 5,908,825 A | 6/1999 | Fasano et al. |
| 5,977,070 A | 11/1999 | Piazza et al. |
| 6,051,555 A | 4/2000 | Hadley |
| 6,054,556 A | 4/2000 | Huby et al. |
| 6,100,048 A | 8/2000 | Cone et al. |
| 6,284,375 B1 | 9/2001 | Jin et al. |
| 6,284,729 B1 | 9/2001 | Bernfield et al. |
| 6,350,430 B1 | 2/2002 | Dooley et al. |
| 6,432,438 B1 | 8/2002 | Shukla |
| 6,476,187 B1 | 11/2002 | Cone et al. |
| 6,534,503 B1 | 3/2003 | Dines et al. |
| 6,579,968 B1 | 6/2003 | Blood et al. |
| 6,608,082 B1 | 8/2003 | Basu et al. |
| 6,613,874 B1 | 9/2003 | Mazur et al. |
| 6,673,767 B1 | 1/2004 | Brodbeck et al. |
| 6,693,165 B2 | 2/2004 | Bednarek |
| 6,716,810 B1 | 4/2004 | Brennan et al. |
| 6,794,489 B2 | 9/2004 | Blood et al. |
| 7,022,674 B2 | 4/2006 | Defelippis et al. |
| 7,049,398 B1 | 5/2006 | Sharma et al. |
| 7,176,279 B2 | 2/2007 | Sharma et al. |
| 7,235,625 B2 | 6/2007 | Diamond et al. |
| 7,342,089 B2 | 3/2008 | Sharma et al. |
| 7,345,144 B2 | 3/2008 | Sharma et al. |
| 7,417,027 B2 | 8/2008 | Sharma et al. |
| 7,473,760 B2 | 1/2009 | Sharma et al. |
| 7,897,721 B2 | 3/2011 | Sharma et al. |
| 8,487,073 B2 | 7/2013 | Shi et al. |
| 9,352,013 B2 | 5/2016 | Spana et al. |
| 9,700,592 B2 | 7/2017 | Spana et al. |
| 10,286,034 B2 | 5/2019 | Spana et al. |
| 11,590,209 B2 * | 2/2023 | Krop .................... A61P 1/00 |
| 2001/0056179 A1 | 12/2001 | Chen et al. |
| 2002/0004512 A1 | 1/2002 | Bakshi et al. |
| 2002/0016291 A1 | 2/2002 | Bednarek |
| 2003/0032791 A1 | 2/2003 | Alan et al. |
| 2003/0083228 A1 | 5/2003 | Carpino et al. |
| 2003/0105024 A1 | 6/2003 | Cone et al. |
| 2003/0113263 A1 | 6/2003 | Marks et al. |

(Continued)

FOREIGN PATENT DOCUMENTS

| | | |
|---|---|---|
| AU | 783718 B2 | 12/2005 |
| AU | 2005249474 A1 | 12/2005 |

(Continued)

OTHER PUBLICATIONS

Goodman and Gilman, "The Pharmacological Basis of Therapeutics", 1992, vol. 1, Ed. 8—International Edition, Chapter 1, p. 8.
Napaporn, J. et al., "Assessment of the Myotoxicity of Pharmaceutical Buffers Using an In Vitro Muscle Model: Effect of pH, Capacity, Tonicity, and Buffer Type," Pharmaceutical Development and Technology, 2000, 5(1):123-130.
Three Month Cumulative Stability Test Results for the pH Stability Study for Bremelanotide, submitted as evidence in the Opposition Procedure in related EP Application No. 13851014, 16 pages. (2013).
Reply of the patent proprietor to the notice(s) of opposition in related EP Application No. 13851014 dated Nov. 11, 2019, 19 pages.

(Continued)

*Primary Examiner* — Jeffrey E. Russel
(74) *Attorney, Agent, or Firm* — Eckert Seamans Cherin & Mellott LLC (57) ABSTRACT

The present invention relates to formulations and methods for treatment of sexual dysfunction in females diagnosed with both sexual dysfunction and controlled hypertension.

19 Claims, 2 Drawing Sheets

(56) References Cited

U.S. PATENT DOCUMENTS

| | | |
|---|---|---|
| 2003/0139384 A1 | 7/2003 | Dudley |
| 2004/0266821 A1 | 12/2004 | Ujjainwalla et al. |
| 2005/0037951 A1 | 2/2005 | Blood et al. |
| 2005/0075344 A1 | 4/2005 | Backer et al. |
| 2005/0222014 A1 | 10/2005 | Diamond et al. |
| 2011/0065652 A1 | 3/2011 | Shi et al. |
| 2014/0378392 A1 | 12/2014 | Spana et al. |
| 2019/0216888 A1 | 7/2019 | Spana et al. |
| 2021/0060120 A1 | 3/2021 | Spana et al. |

FOREIGN PATENT DOCUMENTS

| | | |
|---|---|---|
| AU | 2005269831 A1 | 2/2006 |
| AU | 2005269920 A1 | 2/2006 |
| AU | 2002322466 B2 | 8/2007 |
| AU | 2013337341 A1 | 5/2015 |
| BR | PI0510862 A | 12/2007 |
| BR | 0012200 B1 | 8/2013 |
| BR | 112015009936 A2 | 7/2017 |
| CA | 2453515 A1 | 1/2003 |
| CA | 2568218 A1 | 12/2005 |
| CA | 2573142 A1 | 2/2006 |
| CA | 2574605 A1 | 2/2006 |
| CA | 2376978 C | 11/2012 |
| CA | 2890081 A1 | 5/2014 |
| CN | 1988915 A | 6/2005 |
| CN | 1946494 A | 4/2007 |
| CN | 1988906 A | 6/2007 |
| CN | 101010095 A | 8/2007 |
| CN | 101010096 A | 8/2007 |
| CN | 104755094 A | 7/2015 |
| EP | 0526004 A1 | 2/1993 |
| EP | 0563756 A2 | 10/1993 |
| EP | 0995750 A1 | 4/2000 |
| EP | 0995751 A2 | 4/2000 |
| EP | 1441750 A2 | 8/2004 |
| EP | 1196184 B1 | 4/2005 |
| EP | 1593384 A2 | 11/2005 |
| EP | 1667700 A2 | 6/2006 |
| EP | 1755638 A1 | 2/2007 |
| EP | 1781316 A2 | 5/2007 |
| EP | 1789069 A2 | 5/2007 |
| EP | 2916856 B1 | 9/2018 |
| FR | 2691465 A1 | 11/1993 |
| FR | 2735131 A1 | 12/1996 |
| JP | 2002517444 A | 6/2002 |
| JP | 2003503357 A | 1/2003 |
| JP | 2003534105 A | 11/2003 |
| JP | 2004534851 A | 11/2004 |
| JP | 2008500369 A | 1/2008 |
| JP | 2008505915 A | 2/2008 |
| JP | 2008505917 A | 2/2008 |
| JP | 2008522751 A | 7/2008 |
| JP | 4576493 B2 | 11/2010 |
| JP | 6567971 B2 | 8/2019 |
| KR | 20070036079 A | 4/2007 |
| KR | 101021632 B1 | 3/2011 |
| KR | 20150081345 A | 7/2015 |
| WO | 1993/12095 A1 | 11/1992 |
| WO | 1993/06105 A1 | 4/1993 |
| WO | 1993/07124 A1 | 4/1993 |
| WO | 1993/07149 A1 | 4/1993 |
| WO | 1994/05661 A1 | 3/1994 |
| WO | 1994/22460 A1 | 4/1994 |
| WO | 1995/13086 A1 | 5/1995 |
| WO | 1995/19978 A1 | 7/1995 |
| WO | 1996/26940 A1 | 9/1996 |
| WO | 1996/38471 A1 | 12/1996 |
| WO | 1996/41815 A2 | 12/1996 |
| WO | 1998/10068 A2 | 3/1998 |
| WO | 1998/27113 A2 | 6/1998 |
| WO | 1999/41156 A1 | 2/1999 |
| WO | 1999/21571 A1 | 5/1999 |
| WO | 1999/24433 A1 | 5/1999 |
| WO | 1999/30697 A2 | 6/1999 |
| WO | 1999/43709 A2 | 9/1999 |
| WO | 1999/54333 A1 | 10/1999 |
| WO | 1999/54358 A1 | 10/1999 |
| WO | 1999/55679 A1 | 11/1999 |
| WO | 1999/57148 A1 | 11/1999 |
| WO | 1999/64002 A1 | 12/1999 |
| WO | 1999/66933 A1 | 12/1999 |
| WO | 2000/05263 A2 | 2/2000 |
| WO | 2000/24745 A1 | 5/2000 |
| WO | 2000/35952 A2 | 6/2000 |
| WO | 2000/53148 A2 | 9/2000 |
| WO | 2000/58361 A1 | 10/2000 |
| WO | 2000/74679 A1 | 12/2000 |
| WO | 2001/00224 A1 | 1/2001 |
| WO | 2001/05401 A1 | 1/2001 |
| WO | 2001/10842 A2 | 2/2001 |
| WO | 2001/13112 A1 | 2/2001 |
| WO | 2001/27112 A1 | 4/2001 |
| WO | 2001/27113 A2 | 4/2001 |
| WO | 2001/30808 A1 | 5/2001 |
| WO | 2001/85930 A2 | 11/2001 |
| WO | 2001/90140 A1 | 11/2001 |
| WO | 2002/26774 A2 | 4/2002 |
| WO | 2002/069905 A2 | 9/2002 |
| WO | 2002/085925 A2 | 10/2002 |
| WO | 2003/006604 A2 | 1/2003 |
| WO | 2003/006620 A2 | 1/2003 |
| WO | 2002/064091 A2 | 8/2003 |
| WO | 2004/005324 A2 | 1/2004 |
| WO | 2005/014617 A2 | 2/2005 |
| WO | 2005/079574 A1 | 9/2005 |
| WO | 2005/117935 A1 | 12/2005 |
| WO | 2006/014552 A2 | 2/2006 |
| WO | 2006/014559 A2 | 2/2006 |
| WO | 2009/151714 A1 | 12/2009 |
| WO | 2011/060352 A1 | 5/2011 |
| WO | 2011/133823 A1 | 10/2011 |
| WO | 2014/071339 A2 | 5/2014 |
| WO | 2014/71339 A2 | 5/2014 |
| WO | 2015/03128 A1 | 1/2015 |
| ZA | 200701039 B | 8/2008 |
| ZA | 201503128 B | 11/2016 |

OTHER PUBLICATIONS

Written submission in preparation to/during oral proceedings in the name of Teva Pharmaceuticals in related EP Application No. 13851014 dated Sep. 3, 2020, 13 pages.
Novartis, "Overview of Drug Development", 2008, 18 pages.
Written submission in preparation to/during oral proceedings in the name of Palatin Technologies, Inc. in related EP Application No. 13851014 dated Jan. 26, 2021, 9 pages.
Grounds for the Decision in the Opposition in related EP Application No. 13851014 dated May 4, 2021, 13 pages.
Statement of Grounds for Appeal of the Opposition Decision in related EP Application No. 13851014 dated Aug. 24, 2021, 31 pages.
First Office Action in related CN Application No. 201380056487 dated Jun. 15, 2016, 10 pages.
Second Office Action in related CN Application No. 201380056487 dated May 10, 2017, 10 pages.
Third Office Action in related CN Application No. 201380056487 dated Feb. 26, 2018, 9 pages.
Notice of Reasons for Refusal in related JP Application No. 2015-540853 dated Aug. 1, 2017, 8 pages.
Notice of Reasons for Refusal in related JP Application No. 2015-540853 dated May 22, 2018, 6 pages.
Notice of Reasons for Refusal in related JP Application No. 2015-540853 dated Dec. 18, 2018, 3 pages.
Decision to Grant a Patent in related JP Application No. 2015-540853 dated Jul. 2, 2019, 2 pages.
Communication of Interlocutory decision in Opposition Proceedings for EP 13851014 dated Apr. 5, 2021, 17 pages.
European Search Opinion and Supplementary European Search Report for EP 05769132 dated Dec. 23, 2010, 6 pages.

(56) References Cited

OTHER PUBLICATIONS

European Search Opinion and Supplementary European Search Report for EP 05771593 dated Dec. 27, 2010, 12 pages.
European Search Report for EP 05075914 dated Feb. 17, 2006, 3 pages.
International Search Report and Written Opinion for PCT/US2005/024138 dated Sep. 17, 2006, 5 pages.
International Search Report and Written Opinion for PCT/US2013/068386, dated May 5, 2014, 21 pages.
International Search Report and Written Opinion for PCT/US2005/018739 dated Oct. 3, 2005, 6 pages.
International Search Report and Written Opinion for PCT/US2005/024125 dated Oct. 4, 2006, 5 pages.
International Preliminary Examination Report for PCT/US2002/022196 dated Jul. 1, 2003, 4 pages.
Office Action dated Sep. 6, 2019 for CA 2890081, 5 pages.
Office Action dated Oct. 27, 2020 for CA 2890081, 5 pages.
Office Action dated Mar. 17, 2004 for EP 00950283, 5 pages.
Search Report for JP 2015540853 dated Jul. 26, 2017, 19 pages.
Supplementary European Search Report for EP 04780562 dated Sep. 3, 2009, 6 pages.
Supplementary European Search Report for EP 05761072 dated Jun. 29, 2009, 2 pages.
Supplementary European Search Report for EP 02756458 dated Sep. 1, 2006, 4 pages.
Written Opinion of the Japanese Patent Office for JP 2001505933 dated May 19, 2010, 4 pages.
Written Opinion of the International Searching Authority for PCT/US2004/025749 dated May 24, 2005, 6 pages.
Anderson, K.E. et al., "New Direction for Erectile Dysfunction Therapies" Int. J. Impotence Research, vol. 14, No. Suppl. 1, pp. S82-S92 (2002).
Barn, D.R. et al. "Synthesis of an array of amides by aluminum chloride assisted cleavage of resin-bound esters," Tetrahedron Lett. 37, 3213-3216 (1996).
Bauer, Pharmazeutische Technologie, Georg Thieme Verlag, 1993, Ed. 4, pp. 225-227, 5 pages.
Beckwith B., et al., "The effects of the structure-conformation modifications of melanotropin analogs on learning and memory: D-amino acid substituted linear and cyclic analogs," Peptides, vol. 10, No. 2, pp. 361-368 (1989).
Bednarek M.A. et al., "Structure-function studies on the cyclic peptide MT-II, lactam derivative of α-melanotropin," Peptides, vol. 20:401-09 (1999).
Benelli, A., et al. "Oxytocin Enhances, and Oxytocin Antagonism Decreases, Sexual Receptivity in Intact Female Rats," Neuropeptides, vol. 27, 245-250 (1994).
Brandenburger, Yves, et al., "Synthesis and Receptor Binding Analysis of Thirteen Oligomeric MSH Analogs," J. of Receptor & Signal Transduction Research, vol. 19, No. 1-4, 1999, pp. 467-480.
Catania, A., et al., "α-Melanocyte-stimulating Hormone in Normal Human Physiology and Disease States" Trends in Endocrinology & Metabolism, 2000, 11(8):304-308.
Catania A., et al. "Targeting Melanocortin Receptors as a Novel Strategy to Control Inflammation" Pharmacol. Rev. 56:1-29 (Mar. 2004).
Donlon, John et al. "The Production of Biological Active Peptides in Brain Tissues", Metabolism of Brain Peptides, 1995, CRC Press, Inc., Boca Raton, Florida.
ClinicalTrials.gov, History of Changes for Study: NCT01382719, cited Dec. 6, 2019, https://clinicaltrials.gov/ct2/history/NCT01382719?A=5&B=5&C=merged#StudyPageTo, 12 pp.
DeGrado W.F., et al. Solid-phase synthesis of protected peptides on a polymer bound oxime: Preparation of segments comprising the sequences of a cytotoxic 26-peptide analogue. J. Org. Chem. 47:3258-3261 (1982).
Diamond, "An Effect on the Subjective Sexual Response in Pre-menopausal Women with Sexual Arousal Disorder by Bremelanotide (PT-141), a Melanocortin Receptor Agonist," J. Sex. Med., Vo. 3, 2006, pp. 628-638.
Diamond, L.E. et al., "Double-blind, Placebo-Controlled Evaluation of the Safety, Pharmacokinetic Properties and Pharmacodynamic effects of Intranasal PT-141, a Melanocortin Receptor Agonist, in Healthy Males and Patients with Mild-to-Moderate Erectile Dysfunction," International Journal of Impotence Research, 16:51-59 (2004).
Cragolini, A., et al., "The role of melanocortin receptors in sexual behavior in female rats" Neuropeptides, 2000, 34 (3&4):211-215.
Clayton et al. Bremelanotide for female sexual dysfunctions in premenopausal women: a randomized, placebo-controlled dose-finding trial. Womens Health. May 16, 2016, vol. 12, No. 3, pp. 325-337.
Prescribing Information for VYLEESI (bremelanotide injection), for subcutaneous use. Initial U.S. Approval 2019. Issued Jun. 2019, downloaded Jun. 16, 2022.
White, et al. Usefulness of ambulatory blood pressure monitoring to assess the melanocortin receptor agonist premelanotide. Journal of Hypertension. 2017, vol. 35, pp. 761-768.
Reagan-Shaw et al, Dose translation from animal to human studies revisited, FASEB J., 2007, 22, pp. 659-661.
Body measurements, from http://www.cdc.gov/nchs/fastats/body-measurements.htm, pp. 1-2, accessed Aug. 22, 2023.
Perelman, Clinical Application of CNS-Acting Agents in FSD, J Sex Med, 2007, 4, pp. 280-290.
Agmo, Anders, Animal models of female sexual dysfunction: Basic considerations on drugs, arousal, motivation and behavior, Pharmacology, Biochemistry and Behavior, 122:3-15(2015).
Communication, International Search Report and Written Opinion, PCT/US13/068386, dated May 5, 2014.
Safarinejad, MR, "Evaluation of the Safety and Efficacy of Bremelanotide, a Melanocortin Receptor Agonist, in Female Subjects with Arousal Disorder: A Double-Blind Placebo-Controlled, Fixed Dose, Randomized Study", International Society for Sexual Medicine, 2008, 5:887-897.
E.O. Laumann, A. Paik and R.C. Rosen, Sexual dysfunction in the United States: prevalence and predictors. JAMA J81:537-544 (1999).
J.L. Shifren, B.U. Monz, PA Russo, A. Segreti and C.B. Johannes, Sexual problems and distress in United States women: prevalence and correlates. Obstet Gynecol 112:970-978 (2008).
ML Chivers and R.C. Rosen, Phosphodiesterase type 5 inhibitors and female sexual response: faulty protocols or paradigms? J. Sex. Med. 7:858-72 (2010).
JG. Pfaus, A. Shadiack, T. Van Soest, M. Tse and P. Molinoff, Selective facilitation of sexual solicitation in the female rat by a melanocortin receptor agonist. Proc. Natl. Acad. Sci. USA 101:10201-4 (2004).
J. Pfaus, F. Giuliano and H. Gelez, Bremelanotide: an overview of preclinical CNS effects on female sexual dysfunction. J. Sex. Med. 4:269-279 (2007).
L.E. Diamond, D.C. Earle, J.R. Heiman, R.C. Rosen, MA Perelman and R. Haming, An effect on the subjective sexual response in premenopausal women with sexual arousal disorder by bremelanotide (PT-141), a melanocortin receptor agonist. J. Sex. Med. 3:628-638 (2006).
J.J. Kuo, AA Silva and J.E. Hall, Hypothalamic melanocortin receptors and chronic regulation of arterial pressure and renal function. Hypertension 41:768-774 (2003).
J.J. Kuo, AA da Silva, LS. Tallam and J.E. Hall, Role of adrenergic activity in pressor responses to chronic melanocortin receptor activation. Hypertension 43:370-375 (2004).
J. Nordheim, J.R. Nicholson, K. Dokladny, P. Dunant and K.G. Hofbauer, Cardiovascular responses to melanocortin 4-receptor stimulation in conscious unrestrained normotensive rats. Peptides 27:438-443 (2006).
L.H.T. Van der Ploeg, W.J. Martin, A.O. Howard, R.P. Nargund et al., A role for the melanocortin 4 receptor in sexual function. Proc. Natl. Acad. Sci. USA 99:11381-86 (2002).
A.M. Shadiack, S.D. Sharma, D.C. Earle, C. Spana and T.J. Hallam, Melanocortins in the Treatment of Male and Female Sexual Dysfunction. Current Topics in Medicinal Chemistry 7:1137-1144 (2007).
Palatin Technologies, Inc. "Reports positive bremelanotide study; improved safety profile with subcutaneous administration" PR Newswire, Aug. 12, 2009; [Retrieved Nov. 16, 2017]. Retrieved (56) References Cited

OTHER PUBLICATIONS from the Internet: http://www.pipelinereview.com/index.php/ 2009081228833/Small-Molecules/Pal-atin-Technologies-Inc.-Reports-Positive-Bremelanotide-Study-Improved-Safet- y-Profile-with-Subcutaneous-Administration.html.
Palatin Technologies, Inc. "Bremelanotide in Premenopausal Women With Female Sexual Arousal Disorder and/or Hypoactive Sexual Desire Disorder", ClinicalTrials.gov (NCT01382719), Jun. 27, 2011, clinicaltrials.gov/ct2/history/NCT01382719?V_1= View#StudyPageTop, accessed Mar. 25, 2023.
Supplement European Search Report dated May 24, 2016 for related EP application No. EP 13851014, 9 pages.
Response to Supplement European Search Report dated Dec. 19, 2016 for related EP application No. EP 13851014, 7 pages.
Communication of Intention to Grant dated May 14, 2018 for related EP application No. EP 13851014, 46 pages.
Communication of notice of opposition dated Jul. 1, 2019 from related EP Application No. 13851014.4, 170 pp.
Communication of notices of opposition (R. 79(1) EPC) dated Jul. 2, 2019 from related EP Application No. 13851014.4, 1 pg.
Mathur, D., et al. "PEPlife: A repository of the Half-life of Peptides" Scientific Reports, 2016, 6(36617):1-7.
Koegler, F.H., et al., "Central Melanocortin Receptors Mediate Changes in Food Intake in the Rhesus Macaque" Endocrinology, 2001, 142(6):2586-2592.
Dorr et al., "Evaluation of Melanotan-II, A Superpotent Cyclic Melanotropic Peptide in a Pilot Phase-I Clinical Study," Life Sci. 58:1777-1784 (1996).
Drugs.com, "Palatin Technologies, Inc. Reports Positive Bremelanotide Study; Improved Safety Profile with Subcutaneous Administration," cited Dec. 6, 2019, https://www.drugs.com/clinical_trials/palatin-technologies-inc-reports-positive-bremelanotide-study-improved-safety-profile-subcutaneous-7909.html, 5 pp.
Fan, et al. "Role of melanocortinergic neurons in feeding and the agouti obesity syndrome" Nature 385:1650168 (1997).
Bednarek, M., et al., "Analogs of Lactam Derivatives of α-Melanotropin with Basic and Acid Residues," Biochem. Biophys. Res. Commun., (2000), 272:23-28.
Gantz I. and Fong T. M., The melanocortin system, Am. J. Physiol. Endocrinol. Metab. 284:E468-E474 (2003).
Galande, A. K., et al., "A facile method for the direct synthesis of lanthionine containing cyclic peptides," Lett. Pept. Sci. 8:247 (2002).
Grant, Gregory A., "Protein and Amino Acid Chemistry" Synthetic Peptides: A User's Guide, Washington University School of Medicine, 11-24 (1992).
Gresser, U. and Gleiter, C.H., "Erectile Dysfunction: Comparison of Efficacy and Side Effects of the PDE-5 Inhibitors Sildenafil, Vardenafil, and Tadalafil, Review of the Literature," European J. of Med. res., 7:435-446 (2002).
Hadley, M.E. et al., "Discovery and development of the novel melanogenic drugs," Integration of Pharmaceutical Discovery and Development: Case Studies, edited by Borchardt et al., Plenum Press, New York (1998).
Hadley M.E. et al., "Melanocortin Receptors: Identification and Characterization by Melanotropic Peptide Agonists and Antagonists," Pigment Cell Res, vol. 9:213-34 (1996).
Haskell-Luevano C. et al., "Discovery of Prototype Peptidomimetic Agonists at the Human Melanocortin Receptors MC1R and MC4R," Journal of Medicinal Chemistry, vol. 40:2133-39 (1997).
Hruby, V.J., et al., "Cyclic Lactam α-melanocyte-stimulating Hormone-(4-10)-NH2 with bulky aromatic amino acids at position 7 show high antagonist potency and selectivity at specific melanocortin receptors," Journal of Medicinal Chemistry, vol. 38, No. 18: 3454-61 (1995).
Hruby, V.J., Al-Obeidi, F., and Kazmierski, W. "Emerging approaches in the molecular design of receptor-selective peptide ligands: conformational, topographical and dynamic considerations", Biochem. J. 268:249-262 (1990).

Huszar D., et al. "Targeted disruption of the melanocortin-4 receptor results in obesity in mice." Cell 88:131-141 (1997).
Kaiser, F.E., "Erectile Dysfunction in the Aging Man," Med. Clin. N. Amer. 83:1267-78 (1999).
Kingsberg, "The hypoactive Sexual Desire Disorder Registry to characterize the natural history and outcomes of women with hypoactive sexual desire disorder," Menopause, vol. 19, No. 4, 2012, pp. 379-381.
Löw, Miklós et al. "Role of Chain Termini in Selective Steroidogenic Effect of ACTH/MSH(4-10) on Isolated Adrenocortical Cells", Pepties, 1990, pp. 29-32, vol. 11, No. 1.
Marks, D.L., et al. "Role of the central melanocortin system in cachexia," Cancer Research 61:1432-1438 (Feb. 2001).
Merrifield, Robert B., "Solid Phase Synthesis (Nobel Lecture)", Angewandte Chemie, vol. 24, No. 10, 799-892 (Oct. 1985).
Metabolism of Brain Peptides, Ed. G. O'Cuinn, CRC Press, New York, 1995, pp. 1-9 and 99-101.
MUTSCHLER Mutschler Arzneimittelwirkungen - Lehbuch der Pharmakologie und Toxikologie, Stuttgart: Wissenschaftliche Verlagsgesellschaft mbH, 2001, Ed. 8, pp. 123-124.
Nehra, A et al., "Rationale for Combination Therapy of Intraurethral Prostaglandin E1 and Sildenafil in the Salvage of Erectile Dysfunction Patients Desiring Noninvasive Therapy," International Journal of Impotence Research, 14(S1): S38-S42 (2002).
Haskell-Luevano, C., et al., "β-Methylation of the Phe7 and Trp9 Melanotropin Side Chain Pharmacophores Affects Ligand-Receptor Interactions and Prolonged Biological Activity", J. Med. Chem. (1997), 40:2740-2749.
Notice of opposition to a European patent dated Jun. 18, 2019 from EP Application No. 13851014.4, 21 pp.
Notice of Reasons for Refusal for JP 2003512379 dated Jun. 3, 2008, 4 pages.
Powell, "Compendium of Excipients for Parenteral Formulations," PDA Journal of Pharmaceutical Sciences and Technology, vol. 52, No. 5, Mar. 1998, pp. 238-311.
Pramanick, "Excipient Selection in Parenteral Formulation Development," Pharma Times, vol. 45, No. 3, Mar. 2013, pp. 65-77.
Rosen, R.C., et al., "Evaluation of the safety, pharmacokinetics and pharmacodynamics effects of subcutaneously administered PT-141, a melanocortin receptor agonist, in healthy male subjects and in patients with an inadequate response to Viagra," International Journal of Impotence Research, vol. 16, No. 2, 2004, pp. 135-142.
Rossi, M., et al. "A C-terminal fragment of Agouti-related protein increases feeding and antagonizes the effect of alpha-melanocyte" Endocrinology 139:4428-31 (1998).
Rotella, D.P., et al., "N-3 Substituted Imidazoquinazolinones: Potent and Selective PDE5 Inhibitors as Potential Agents for Treatment of Erectile Dysfunction" J. Med. Chem., 43:1257-1263 (2000).
Roubenoff R., "The pathophysiology of wasting in the elderly." J. Nutr. 129 (1S Suppl.):256S-259S (1999).
Schiöth H.B., et al., "Discovery of novel melanocortin4 receptor selective MSH analogues," British Journal of Pharmacology, vol. 124:75-82 (1998).
Schiöth H.B., et al., "Selective properties of C-and N-terminals and core residues of the melanocyte-stimulating hormone on binding to the human melanocortin receptor subtypes," European Journal of Pharmacology, vol. 349:359-66 (1998).
Seely, R.J. et al., "The role of CNS glucagons-like peptide-1 (7-36) amide receptors in mediating the visceral illness effects of lithium chloride." J. Neurosci. 20:1616-1621 (2000).
Sommer, F. and Engelmann, U., "Future Options for Combination Therapy in the Management of Erectile Dysfunction In Older Men" Drugs and Aging, 9:555-564 (2004).
Sourverein, P.C. et al., "Incidence and Determinants of Sildenafil (dis)continuation: the Dutch Cohort of Sildenafil Users," International Journal of Impotence Research 14:259-265 (2002).
Spiegel, "Use of Nonaqueous Solvents in Parental Products," Journal of Pharmaceutical Sciences, vol. 52, No. 10, 1963, pp. 917-927.
Skuladottir, G., et al., "Long term orexigenic effect of a novel melanocortin 4 receptor selective antagonist," Br. J. Pharmacol., (1999), 126:27-34.
Toniolo, C., "Conformationally restricted peptides through short-range cyclizations", Int. J. Peptide Protein Res. 35:287-300 (1990).

(56) References Cited

OTHER PUBLICATIONS

Van der Ploeg, L.H.T. et al, "A Role for the Melanocortin 4 Receptor in Sexual Function." P.N.A.S., 99 (17):11381-11386 (Aug. 2002).
Vemulapalli et al., "Activation of Central Melanocortin Receptors by MT-II Increases Cavernosal Pressure in Rabbits by the Neuronal Release of NO" British Journal of Pharmacology, 134:1705-1710 (2001).
Wessells H. et al., "Synthetic Melanotropic peptide initiates erections in men with psychogenic erectile dysfunction: double-blind, placebo controlled crossover study," Journal of Urology, vol. 160(2):389-393 (Aug. 1998).
Wessells, H. et al., "Effect of an Alpha-Melanocyte Stimulating Hormone Analog on Penile Erection and Sexual Desire In Men with Organic Erectile Dysfunction" Urology 56:641-646 (2000).
Wessells, H. et al., "Melanocortin receptor agonists, penile erection, and sexual motivation: human studies with Melanotan II," Intl. J. Impotence. Res. 12:S74-S79 (2000).
Wisse, B.E. et al., "Reversal of cancer anorexia by blockade of central melanocortin receptors in rats." Endocrinology 142:3292-3301 (2001).
Yang, Y. et al., "Molecular determinants of ligand binding to the human melanocortin-4 receptor," Biochemistry, vol. 39, No. 48, p. 14900-14911 (Dec. 5, 2000).
Youngquist et al. "Generation and screening of combinatorial peptide libraries designed for rapid sequencing by mass spectrometry" J. of Am. Chem. Soc. vol. 117, No. 14: Apr. 12, 1995, pp. 3900-3906.
Rowe, F. and Sarkies, N., "The relationship between obesity and idiopathic intracranial hypertension." International Journal of Obesity, 1999, 23(1):54-59.
Vergoni, A.V., et al., "Chronic melanocortin 4 receptor blockage causes obesity without influencing sexual behavior in male rats." Journal of Endocrinology, 2000, 166:419-426.

\* cited by examiner

Figure 1:

| | Study AMAG-101 Day -1 (Placebo) | | | Study AMAG-101 Day 8 (After 8 days of daily dosing: BMT 1.75 mg) | | | | | | Study AMAG-101 Day 16 (After 16 days of daily dosing: BMT 1.75 mg) | | | | | | Study AMAG-101 Day 16 (After 16 days of daily dosing: Placebo) | | | | | |
|---|---|---|---|---|---|---|---|---|---|---|---|---|---|---|---|---|---|---|---|---|---|
| | 24 hour | Daytime | Nighttime | 24 hour | Change from Placebo Period | Daytime | Change from Placebo Period | Nighttime | Change from Placebo Period | 24 hour | Change from Placebo Period | Daytime | Change from Placebo Period | Nighttime | Change from Placebo Period | 24 hour | Change from Placebo Period | Daytime | Change from Placebo Period | Nighttime | Change from Placebo Period |
| SBP | 109.0 (8.07) | 112.4 (8.21) | 102.4 (9.38) | 110.1 (8.17) | +1.07 (4.47) | 114.3 (8.46) | +1.87 (4.96) | 101.8 (8.91) | -0.57 (5.57) | 108.8 (7.12) | -0.43 (4.84) | 112.8 (7.47) | +0.43 (5.29) | 100.4 (8.26) | -2.46 (5.90) | 106.9 (8.32) | -2.28 (4.22) | 110.9 (8.11) | -1.84 (5.36) | 99.1 (9.86) | -3.57 (5.58) |
| DBP | 69.6 (5.79) | 72.7 (6.12) | 63.5 (6.84) | 70.5 (6.00) | +1.05 (3.77) | 74.3 (6.35) | +1.65 (4.22) | 63.2 (6.66) | -0.15 (4.84) | 70.3 (5.63) | +0.65 (3.73) | 74.2 (5.93) | +1.40 (4.02) | 62.4 (6.44) | -1.00 (4.94) | 68.1 (5.45) | -1.30 (3.93) | 71.8 (5.75) | -0.54 (4.36) | 60.9 (6.26) | -2.98 (4.86) |
| HR | 77.9 (8.12) | 80.4 (8.35) | 73.0 (8.88) | 77.9 (9.00) | -0.18 (5.77) | 80.2 (9.53) | -0.47 (6.50) | 73.4 (9.09) | +0.33 (6.43) | 78.3 (8.15) | -0.48 (6.52) | 79.4 (8.27) | -1.79 (6.27) | 74.2 (8.22) | +0.04 (7.95) | 78.7 (9.57) | +1.20 (6.74) | 80.7 (9.46) | +0.34 (7.14) | 72.0 (9.94) | +0.02 (7.43) |

|  | Study BMT-101 (single, acute dose, co-administered with steady state anti-hypertensive medication) DAY -1 BASELINE (ANTI-HTN MEDS ONLY) | | | Study BMT-101 (single, acute dose, co-administered with steady state anti-hypertensive medication) BMT 1.75 mg | | | Study BMT-101 (single, acute dose, co-administered with steady state anti-hypertensive medication) Placebo | | | CHANGE (BMT MINUS PLACEBO) | | |
|---|---|---|---|---|---|---|---|---|---|---|---|---|
|  | 24 hour | Daytime | Nighttime | 24 hour | Daytime | Nighttime | 24 hour | Daytime | Nighttime | 24 hour | Daytime | Nighttime |
| Panel A: HCTZ 12.5 mg (diuretic) | | | | | | | | | | | | |
| SBP | 113.08 (7.89) | 113.92 (8.11) | 107.22 (7.47) | 115.03 (7.21) | 115.71 (7.33) | 110.21 (7.91) | 111.27 (6.34) | 112.18 (6.62) | 104.72 (6.64) | +3.76 (3.11) | +3.53 (3.11) | +5.49 (6.36) |
| DBP | 69.99 (7.43) | 70.97 (7.425) | 63.26 (7.18) | 71.92 (5.86) | 72.60 (5.88) | 66.89 (6.54) | 69.07 (5.83) | 70.02 (6.17) | 62.24 (5.20) | +2.84 (2.72) | +2.58 (2.67) | +4.64 (5.85) |
| HR | 71.95 (9.41) | 72.67 (9.44) | 66.92 (10.45) | 70.71 (8.89) | 70.88 (8.99) | 69.58 (8.86) | 72.01 (9.37) | 72.69 (9.44) | 67.07 (9.86) | -1.30 (4.34) | -1.81 (4.36) | +2.52 (5.82) |
| Panel B: Metoprolol 50 mg (beta-blocker) | | | | | | | | | | | | |
| SBP | 114.85 (11.87) | 116.02 (11.99) | 106.73 (13.14) | 110.88 (11.15) | 111.73 (11.25) | 104.73 (12.79) | 107.39 (10.34) | 107.92 (10.46) | 103.62 (11.26) | +3.49 (4.68) | +3.81 (5.10) | +1.11 (5.77) |
| DBP | 72.08 (7.75) | 73.12 (7.89) | 64.80 (8.68) | 67.65 (7.08) | 68.46 (7.23) | 61.76 (7.81) | 65.80 (6.75) | 66.42 (6.86) | 61.42 (7.39) | +1.84 (2.63) | +2.04 (2.79) | +0.34 (5.07) |
| HR | 71.50 (6.42) | 72.48 (6.78) | 64.71 (5.77) | 59.51 (6.31) | 59.38 (6.37) | 60.45 (6.48) | 62.04 (6.92) | 62.09 (6.95) | 61.64 (7.36) | -2.53 (3.13) | -2.71 (3.19) | -1.19 (4.37) |
| Panel C: Amlodipine 5 mg (calcium channel blocker) | | | | | | | | | | | | |
| SBP | 111.97 (8.44) | 112.78 (8.44) | 106.45 (10.10) | 112.53 (7.38) | 113.59 (7.74) | 105.18 (6.99) | 110.83 (6.65) | 111.77 (6.66) | 103.92 (8.10) | +1.71 (2.60) | +1.81 (2.65) | +1.26 (4.59) |
| DBP | 68.60 (6.68) | 69.41 (6.67) | 63.08 (7.84) | 69.00 (5.28) | 70.00 (5.62) | 62.09 (5.06) | 66.71 (5.41) | 67.67 (5.49) | 59.75 (6.71) | +2.29 (1.93) | +2.32 (2.01) | +2.35 (4.51) |
| HR | 71.35 (6.25) | 72.16 (6.46) | 65.69 (5.82) | 73.00 (6.74) | 73.24 (6.83) | 71.27 (7.33) | 75.22 (7.45) | 75.84 (7.69) | 70.75 (7.49) | -2.23 (3.08) | -2.59 (3.47) | +0.52 (3.49) |
| Panel D: Lisinopril 10 mg (ACE inhibitor) | | | | | | | | | | | | |
| SBP | 109.82 (5.38) | 110.68 (5.21) | 103.9 (9.06) | 107.39 (7.38) | 108.35 (7.30) | 100.44 (9.25) | 104.01 (8.04) | 104.82 (8.25) | 98.51 (8.58) | +3.38 (3.27) | +3.53 (3.19) | +1.93 (6.21) |
| DBP | 67.33 (5.81) | 68.18 (5.85) | 61.49 (7.09) | 65.08 (4.75) | 65.91 (4.82) | 59.14 (6.72) | 62.20 (5.40) | 62.99 (5.57) | 56.76 (6.84) | +2.89 (2.82) | +2.91 (2.74) | +2.37 (6.20) |
| HR | 72.43 (6.69) | 73.26 (6.80) | 66.79 (7.13) | 71.59 (7.13) | 71.74 (7.07) | 70.45 (8.07) | 73.99 (7.01) | 74.70 (7.14) | 69.23 (8.45) | -2.40 (3.96) | -2.96 (4.23) | +1.22 (5.16) |
| Panel E: Losartan 50 mg (angiotensin receptor blocker) | | | | | | | | | | | | |
| SBP | 113.57 (11.49) | 114.43 (11.74) | 107.89 (11.01) | 110.10 (9.98) | 111.07 (9.92) | 103.02 (12.09) | 107.93 (8.16) | 108.72 (8.36) | 102.05 (8.91) | +2.42 (3.55) | +2.66 (3.47) | +0.83 (7.04) |
| DBP | 68.19 (7.99) | 68.98 (8.08) | 62.92 (7.98) | 64.93 (7.41) | 65.94 (7.50) | 57.35 (8.10) | 63.31 (6.68) | 64.16 (7.04) | 57.32 (6.46) | +1.88 (1.98) | +2.10 (2.34) | -0.12 (4.05) |
| HR | 71.71 (8.68) | 72.43 (8.67) | 66.97 (9.47) | 70.81 (7.50) | 70.93 (7.43) | 69.90 (9.33) | 72.55 (7.57) | 72.94 (7.51) | 69.93 (8.99) | -2.19 (3.15) | -2.44 (3.41) | -0.50 (4.51) |

Figure 2

USE OF BREMELANOTIDE IN PATIENTS WITH CONTROLLED HYPERTENSION

CROSS-REFERENCE TO RELATED APPLICATIONS

This application is a Continuation of U.S. application Ser. No. 17/154,593, filed Jan. 21, 2021, which claims priority to U.S. Provisional Application No. 62/963,719, filed Jan. 21, 2020, the entire contents of which are incorporated herein by reference.

FIELD OF THE INVENTION

The present invention relates to formulations and methods for treatment of sexual dysfunction in females diagnosed with both sexual dysfunction and controlled hypertension.

BACKGROUND OF THE INVENTION

It is known that agonists of the melanocortin receptor, and particular melanocortin 4 receptor (MC4-R) agonists, may be employed for treatment of sexual dysfunction. The cyclic, heptapeptide melanocortin receptor agonist Ac-Nle-cyclo(-Asp-His -D-Phe-Arg-Trp-Lys)-OH, with the USAN adopted name bremelanotide and formerly known as PT-141, as further disclosed in U.S. Pat. Nos. 6,579,968 and 6,794,489, has been employed in clinical trials for sexual dysfunction.

It has been reported in the literature that MC4-R agonists induce an adrenergic response, resulting in an increase in blood pressure and heart rate. See, for example, J. J. Kuo, A. A. Silva and J. E. Hall, Hypothalamic melanocortin receptors and chronic regulation of arterial pressure and renal function. Hypertension 41:768-774 (2003); J. J. Kuo,A. A. da Silva, L. S. Tallam and J. E. Hall, Role of adrenergic activityin activity in pressor responses to chronic melanocortin receptor activation. Hypertension 43:370-375 (2004); U. Nordheim, J. R. Nicholson, K.Dokladny, P. Dunant and K. G. Hofbauer, Cardiovascular responses to melanocortin 4-receptor stimulation in conscious unrestrained normotensive rats. Peptides 27:438-443 (2006).

Adverse events have been observed with melanocortin agonists, including bremelanotide, primarily relating to an increase in blood pressure, and nausea and vomiting. Indeed, the FDA was particularly concerned with the impact of bremelanotide on individuals with hypertension. The FDA determined the blood pressure data from the phase 3 trials (studies 301 and 302) were limited because they did not evaluate BP effects with daily bremelanotide use, did not include ambulatory blood pressure monitoring, and excluded subjects from therapy with elevated blood pressure. The FDA further found that Study 54 (White W B. *J Hypertens*. 2017; 35:761-768) was limited by (1) the relatively selective population, without significant cardiovascular risk factors; (2) evidence that the BP effect had not resolved by 24 hours and may, therefore, persist longer than 24 hours; and (3) absence of data following long-term repeat use of bremelanotide. As the safety of bremelanotide in patients diagnosed with both female sexual dysfunction and controlled hypertension was unknown, the FDA required a more detailed study using ambulatory blood pressure monitoring to better understand the blood pressure effects of bremelanotide for the proposed indication and population.

The present inventors have determined that patients diagnosed with both female sexual dysfunction and controlled hypertension may safely treat the female sexual dysfunction with bremelanotide, as detailed below.

BRIEF SUMMARY OF THE INVENTION

One aspect of the present disclosure encompasses a method for treating female sexual dysfunction in a female patient diagnosed with both female sexual dysfunction and controlled hypertension, said method comprising administering more than a single subcutaneous injection of a composition comprising bremelanotide or a pharmaceutically acceptable salt of bremelanotide to the female patient, when the patient is anticipating sexual activity, wherein the composition comprises 1.00 mg to 1.75 mg net peptide weight of bremelanotide, and wherein only one injection is administered within 24 hours, and no more than eight injections are administered in a month, thereby treating female sexual dysfunction.

Another aspect of the present disclosure encompasses a method for treating female sexual dysfunction in a female patient diagnosed with both female sexual dysfunction and controlled hypertension, said method comprising administering more than a single subcutaneous injection of a composition comprising bremelanotide or a pharmaceutically acceptable salt of bremelanotide to the female patient, when the patient is anticipating sexual activity, the composition comprising an amount of bremelanotide sufficient to result in a peak plasma concentration of bremelanotide of no more than 120 ng/mL within 60 minutes after administration of the composition, and wherein only one injection is administered within 24 hours, and no more than eight injections are administered in a month, thereby treating female sexual dysfunction.

Yet another aspect of the present disclosure encompasses a method for treating female sexual dysfunction in a female patient diagnosed with both female sexual dysfunction and controlled hypertension, said method comprising administering more than a single subcutaneous injection of a composition comprising bremelanotide or a pharmaceutically acceptable salt of bremelanotide to the female patient, when the patient is anticipating sexual activity, the composition comprising an amount of bremelanotide sufficient to result in a peak plasma concentration of bremelanotide of no more than 120 ng/mL within 60 minutes after administration of the composition, wherein the composition comprises 1.00 mg to 1.75 mg net peptide weight of bremelanotide, and wherein only one injection is administered within 24 hours, and no more than eight injections are administered in a month, thereby treating female sexual dysfunction.

A further aspect of the present disclosure encompasses a method for treating female sexual dysfunction in a female patient diagnosed with both female sexual dysfunction and controlled hypertension, said method comprising administering more than a single subcutaneous injection of a composition comprising bremelanotide or a pharmaceutically acceptable salt of bremelanotide to the female patient, when the patient is anticipating sexual activity, wherein the composition comprises 1.00 mg to 1.75 mg net peptide weight of bremelanotide, and wherein only one injection is administered within 24 hours, and no more than sixteen injections are administered on consecutive days, thereby treating female sexual dysfunction.

A still further aspect of the present disclosure encompasses a method for treating female sexual dysfunction in a female patient diagnosed with both female sexual dysfunction and controlled hypertension, said method comprising administering more than a single subcutaneous injection of a composition comprising bremelanotide or a pharmaceutically acceptable salt of bremelanotide to the female patient, when the patient is anticipating sexual activity, the composition comprising an amount of bremelanotide sufficient to result in a peak plasma concentration of bremelanotide of no more than 120 ng/mL within 60 minutes after administration of the composition, and wherein only one injection is administered within 24 hours, and no more than sixteen injections are administered on consecutive days, thereby treating female sexual dysfunction.

Still another aspect of the present invention encompasses a method for treating female sexual dysfunction in a female patient diagnosed with both female sexual dysfunction and controlled hypertension, said method comprising administering more than a single subcutaneous injection of a composition comprising bremelanotide or a pharmaceutically acceptable salt of bremelanotide to the female patient, when the patient is anticipating sexual activity, the composition comprising an amount of bremelanotide sufficient to result in a peak plasma concentration of bremelanotide of no more than 120 ng/mL within 60 minutes after administration of the composition, wherein the composition comprises 1.00 mg to 1.75 mg net peptide weight of bremelanotide, and wherein only one injection is administered within 24 hours, and no more than sixteen injections are administered consecutively, thereby treating female sexual dysfunction.

Other aspects and novel features, and further scope of applicability of the present disclosure will be set forth in part in the detailed description to follow, taken in conjunction with the accompanying drawings, and in part will become apparent to those skilled in the art upon examination of the following, or may be learned by practice of the invention.

BRIEF DESCRIPTION OF THE FIGURES

FIG. 2 depicts a table displaying the data from the co-administration of bremelanotide with an anti-hypertensive agent.

DETAILED DESCRIPTION

Definitions

Before proceeding with the description of the invention, certain terms are defined as set forth herein.

The "amino acid" and "amino acids" used in this invention, and the terms as used in the specification and claims, include the known naturally occurring protein amino acids, which are referred to by both their common three letter abbreviation and single letter abbreviation. See generally Synthetic Peptides: A Users Guide, G. A. Grant, editor, W.H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in Synthetic Peptides: A User's Guide, cited above; V. J. Hruby, F. Al-Obeidi and W.Kazmierski: Biochem. J. 268:249-262, 1990; and C. Toniolo: Int. J.Peptide Protein Res. 35:287-300, 1990; the teachings of all of which are incorporated herein by reference.

In the listing of compounds according to the present invention, the amino acid residues have their conventional meaning as given in Chapter 2400 of the Manual of Patent Examining Procedure, 8th Ed. Thus,"Nle" is norleucine; "Asp" is aspartic acid; "His" is histidine; "D-Phe" is D-phenylalanine; "Arg" is arginine; "Trp" is tryptophan; and "Lys" is lysine; "Ac" refers to a peptide or amino acid sequence that is acetylated [($CH_3$)—CO—].

The term "composition", as in pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions utilized in the present invention encompass any composition made by admixing an active ingredient and one or more pharmaceutically acceptable carriers.

The phrase "controlled hypertension" refers to patients who were diagnosed with hypertension (any stage) or elevated blood pressure, and who, via one or more interventions, have consistently maintained their systolic blood pressure below 130 mm Hg or their diastolic blood pressure below 80 mm Hg. Interventions may include, for example, pharmaceutical interventions or life-style interventions. As used herein, "elevated blood pressure" is defined as a systolic blood pressure between 120 and 129, and a diastolic blood pressure less than 80 (see, for instance, Wheaton et al. High Bool Pressure Clinical Practice Guide, J. Amer. Col. Cardiology, vol. 71, no. 19, 2018, e138).

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes ED in a male mammal and FSD in a female mammal. "Erectile dysfunction" (ED) is a disorder involving the failure of a male mammal to achieve functional erection, ejaculation, or both. Erectile dysfunction is accordingly synonymous with impotence, and includes the inability to attain or sustain an erection of sufficient rigidity for coitus.

"Female sexual dysfunction" (FSD) is recognized in DSM-IV as four major disorders that define FSD: decreased sexual desire, decreased sexual arousal, dyspareunia, and difficulty in achieving orgasm. For purposes of diagnosis and therapy, FSD may be further defined to include female sexual arousal disorder (FSAD) and hypoactive sexual desire disorder (HSDD). The Draft Guidance for Industry, Female Sexual Dysfunction: Clinical Development of Drug Products for Treatment, U.S. Food and Drug Administration, May 2000, lists four recognized components of FSD: decreased sexual desire; decreased sexual arousal; dyspareunia; and persistent difficulty in achieving or inability to achieve orgasm, with the components associated with personal distress, as determined by the affected woman. Sexual dysfunction in females can also include inhibited orgasm and dyspareunia, which is painful or difficult coitus. Female sexual dysfunction includes, but is not limited to, a number of categories of diseases, conditions and disorders including HSDD, sexual anhedonia, sexual arousal disorder, dyspareunia and vaginismus. Hypoactive sexual desire disorder includes a disorder in which sexual thoughts or fantasies and/or desire for sexual activity are persistently or recurrently diminished or absent, causing marked distress or interpersonal difficulties, and which cannot be attributed to a coexisting medical or psychiatric condition, problems with the relationship, or effects of a medication or drug substance. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

In clinical trials to determine the efficacy of drugs and therapies for treatment of FSD, any of a number of validated patient-reported outcome questionnaires are utilized. These may include:

FSEP-R Female Sexual Encounter Profile—Revised,
FSDS-DAO Female Sexual Distress Scale—Desire/Arousal/Orgasm,
FSFI Female Sexual Function Index,
GAQ General Assessment Questions,
SIDI-F Sexual Interest and Desire Inventory—Female, or
WITS-9 Women's Inventory of Treatment Satisfaction Electronic diary devices can be employed for use by subjects to complete questionnaires, including but not limited to the FSEP-R questionnaire, which can be completed outside of the clinic (at home) following a sexual encounter.

By a melanocortin receptor "agonist" is meant an endogenous or drug substance or compound, including a compound such as bremelanotide, which can interact with a melanocortin receptor and initiate a pharmacological response, including but not limited to adenyl cyclase expression, characteristic of the melanocortin receptor.

By the abbreviation "% CV" is meant the coefficient of variation, which is the ratio of the standard deviation (SD) to the mean expressed as a percentage. In one embodiment of the present disclosure, the variability in peak plasma concentration within 60 minutes after subcutaneous injection administration is a % CV less than about 30, or alternatively less than about 25, or alternatively less than about 20. The variability in peak plasma concentration within 60 minutes after intranasal administration is a % CV greater than about 25, or alternatively greater than about 30, or alternatively greater than about 40, or alternatively greater than about 50, or alternatively greater than about 60, or alternatively greater than about 70.

In the specification and claims, where there is a reference to a weight of bremelanotide or a pharmaceutically acceptable salt of bremelanotide per dose (such as, e.g., administering a dose of 1.75 mg bremelanotide or a pharmaceutically acceptable salt of bremelanotide), it is to be understood that such weight is net peptide weight, that is, net of the salt in the instance of a pharmaceutically acceptable salt.

The methods and pharmaceutical compositions disclosed herein can be used for both medical applications and animal husbandry or veterinary applications. Typically, the methods are used in humans, including specifically female humans, but may also be used in other mammals. The term "patient" is intended to denote a mammalian individual, and is so used throughout the specification. The primary applications of this invention involve human female patients, but this invention may be applied to laboratory, farm, zoo, wildlife, pet, sport or other animals.

I. Compounds and Compositions of the Invention.

In a preferred embodiment of the present invention, the melanocortin receptor agonist is: Ac-Nle-cyclo(-Asp-His-D-Phe-Arg-Trp-Lys)-OH (bremelanotide). The peptide of bremelanotide has a formula of $C_{50}H_{68}N_{14}O_{10}$, and a net molecular weight of 1025.18. This peptide may be synthesized by conventional means, including either solid-phase or liquid-phase techniques, and purified to (e.g., to greater than 99% purity) by HPLC, yielding a white powder that is a clear, colorless solution in water. An exemplary synthesis of bremelanotide is disclosed in U.S. Pat. No. 6,579,968. The structure of bremelanotide is:

In one embodiment of the invention, bremelanotide is synthesized by solid-phase synthesis and purified according to methods known in the art. Any of a number of well-known procedures utilizing a variety of resins and reagents may be used to prepare bremelanotide.

Bremelanotide may be in the form of any pharmaceutically acceptable salt. Acid addition salts of the compounds of this invention are prepared in a suitable solvent from the peptide and an excess of an acid, such as hydrochloric, hydrobromic, sulfuric, phosphoric, acetic, trifluoroacetic, maleic, citric, tartaric, oxalic, succinic or methanesulfonic acid. In one embodiment, the pharmaceutically acceptable salt is the acetate salt form of bremelanotide.

In a preferred embodiment, bremelanotide is an acetate salt form, and is formulated in a buffered aqueous solution including glycerin, and prepackaged in a syringe and auto-injector device. In alternative embodiments, bremelanotide is any pharmaceutically acceptable salt form, and is formulated in any pharmaceutically acceptable aqueous solution, the aqueous solution optionally including one or more salts, such as sodium chloride, one or more acids, such as citric acid, and one or more additional ingredients, including cellulose or derivatives thereof, saccharides or polysaccharides such as dextrose, and any of a wide variety of surfactants, chelating agents and preservatives.

The following is a list of all components used in the manufacture of an exemplary drug product:
Bremelanotide API
Glycerin, USP vegetable grade
Hydrochloric Acid, NF (if needed) for pH adjustment
Sodium Hydroxide, NF (if needed) for pH adjustment
Water for Injection, USP or Sterile Water for Injection, USP

TABLE 1

Quantitative Composition of Bremelanotide Injection Drug Product

| Component and Function | Bremelanotide Injection (Quantity in each syringe) | | |
|---|---|---|---|
| | 0.75 mg/0.3 mL (2.50 mg/mL) | 1.25 mg/0.3 mL (4.17 mg/mL) | 1.75 mg/0.3 mL (5.83 mg/mL) |
| Bremelanotide API* | 0.75 mg | 1.25 mg | 1.75 mg |
| Glycerin, USP, vegetable grade [tonicity agent] | 7.5 mg | 7.5 mg | 7.5 mg |
| Hydrochloric Acid, NF [to adjust pH] | To adjust pH | To adjust pH | To adjust pH |
| Sodium Hydroxide, NF [to adjust pH] | To adjust pH | To adjust pH | To adjust pH |
| Water For Injection, USP [diluent and solubilizing agent] | QS to 0.3 mL | QS to 0.3 mL | QS to 0.3 mL |

*Net bremelanotide (anhydrous, free base equivalent)

The bremelanotide drug product for subcutaneous injection is packaged in single-use pre-filled syringes with Flurotec plunger stoppers, a plunger rod for actuation, and a plastic safety device. The package components are further described below:
Syringe: BD HypakSCF 1 mL Long Syringe Barrel with 29G.times.½" 5 Bevel needle, Formulation BD260 (Primary container closure, Sterile, Clean and Ready-to-fill) (BD, Franklin Lakes, N.J., US)
Stopper: BD HypakNSCF 1 mL Long Plunger Stopper, Formulation W4023 Flurotec Daikyo Coated (Primary container closure, Sterile, Clean and Ready-to-fill) (BD, Franklin Lakes, N.J., US)
Plunger rod: BD Hypak 1 mL Long PlungerRod Polypropylene (Lies outside primary container closure, non-sterile). (BD, Franklin Lakes, N.J., US) [0091] Auto-Injector: YpsoMate, automatic injection device for pre-filled syringe manufactured by Ypsomed (Burgdorf, Switzerland)

II. Use of Prefilled Syringes and Auto-Injector Devices

In one aspect, a prefilled syringe may be utilized, optionally with an auto-injector device, permitting a patient to rapidly and simply self-administer a subcutaneous dose of bremelanotide. For example, bremelanotide injection, a parenteral drug product for subcutaneous injection, is formulated in an aqueous system containing 2.5% w/v glycerin at pH 5. It is packaged in single-use Type I glass 1 mL prefilled syringes with staked one-half inch 29 gauge needles fitted with a needle shield and closed with gray Flurotec plunger stoppers. The primary container is secondarily fitted with a plunger rod for actuation and a safety device to prevent accidental access to the needle after use. Each unit is filled to deliver a minimum volume of 0.3 mL.

III. Uses and Methods of the Disclosure

It was unclear following previous clinical studies of bremelanotide if extended dosing (e.g. more than a single dose) of subcutaneous bremelanotide to females diagnosed with FSD would provoke dangerous or sustained increases in blood pressure. The present inventors have determined that for treatment regimes that restrict dosing to no more than one subcutaneous injection every 24 hours, and no more than sixteen consecutive daily administrations, subcutaneous injections of bremelanotide are safe and efficacious for treating FSD in patients with controlled hypertension. In some embodiments, the female patient with controlled hypertension has consistently maintained their systolic blood pressure below 130 mm Hg and their diastolic blood pressure below 80 mm Hg. In certain embodiments, the female patient with controlled hypertension has elevated blood pressure.

In one embodiment, the present disclosure provides a method for treating FSD in a female patient diagnosed with both FSD and controlled hypertension and anticipating sexual activity, comprising administering more than a single subcutaneous injection to the female patient of a composition comprising no more than about 1.75 mg of bremelanotide or a pharmaceutically acceptable salt of bremelanotide, thereby treating FSD. In particular embodiments, two, three, four, five, six, seven, eight, nine, ten, eleven, twelve, thirteen, fourteen, fifteen, or sixteen subcutaneous injections are administered to the patient, with at least 24 hours between each injection. In other embodiments, no more than eight subcutaneous injections are administered within a month, with at least 24 hours between each injection.

In one embodiment of this method, no more than 1.25 mg of bremelanotide or a pharmaceutically acceptable salt of bremelanotide is administered by subcutaneous injection. In another embodiment, between about 1.00 and 1.75 mg of bremelanotide or a pharmaceutically acceptable salt of bremelanotide is administered with each injection. In yet another embodiment, between about 1.25 and 1.75 mg of bremelanotide or a pharmaceutically acceptable salt of bremelanotide is administered with each injection. In yet another embodiment, 1.75 mg of bremelanotide or a pharmaceutically acceptable salt of bremelanotide is administered with each injection.

The composition for each subcutaneous injection may be an aqueous solution comprising acetate salt of bremelanotide and glycerin. In one embodiment, the composition is an aqueous solution consisting essentially of acetate salt of bremelanotide and 2.5% glycerin (w/v). The acetate salt of bremelanotide may be between about 6% and 12% (w/w) acetic acid in an aqueous solution of bremelanotide. In one embodiment, the composition is at a pH of about 5.0, and further comprises agents to adjust pH, which agents to adjust pH may comprise, without limitation, hydrochloric acid and sodium hydroxide.

The disclosure further provides for use of a formulation dose comprising no more than about 1.75 mg of bremelanotide or a pharmaceutically acceptable salt of bremelanotide in the manufacture of a subcutaneous injectable medicament for the treatment of FSD in a female patient diagnosed with both FSD and controlled hypertension and anticipating sexual activity. In a related embodiment, the formulation dose comprises between about 1.00 and 1.75 mg of bremelanotide or a pharmaceutically acceptable salt of bremelanotide, or between about 1.25 and 1.75 mg of bremelanotide or a pharmaceutically acceptable salt of bremelanotide for each injection.

In another embodiment the invention provides a prefilled dose unit comprising an aqueous solution of acetate salt of no more than about 1.75 mg of bremelanotide. The prefilled dose unit may include a prefilled syringe, or may include a cartridge adapted for use in a subcutaneous administration drug delivery device.

In yet another embodiment, the invention provides a method for treating FSD in a female patient diagnosed with both FSD and controlled hypertension and anticipating sexual activity, comprising administering more than a single subcutaneous injection of a composition comprising bremelanotide or a pharmaceutically acceptable salt of bremelanotide in an amount sufficient to result in a peak plasma concentration within 60 minutes after administration of bremelanotide in the female patient of no more than about 120 ng/mL, thereby treating FSD. In particular embodiments, two, three, four, five, six, seven, eight, nine, ten, eleven, twelve, thirteen, fourteen, fifteen, or sixteen subcutaneous injections are administered to the patient, with at least 24 hours between each injection. In other embodiments, no more than eight subcutaneous injections are administered within 30 days (a month), with at least 24 hours between each injection.

In each of the above embodiments, treating FSD may be indicated by an increase in frequency of satisfying sexual events upon administration of the bremelanotide or pharmaceutically acceptable salt thereof, or by improved overall sexual function, including where improved overall sexual function is measured by the Female Sexual Function Index, such as a Female Sexual Function Index total score improvement of 3 or greater. Increased efficacy may also be indicated by reduced associated distress related to sexual dysfunction, including where reduced associated distress related to sexual dysfunction is measured by the Female Sexual Distress Scale-DAO.

In each of the above embodiments, the FSD is hypoactive sexual desire disorder (HSDD). In some embodiments, the FSD is acquired, generalized HSDD as characterized by low sexual desire that causes marked distress or interpersonal difficulty. In some embodiments, the FSD is acquired, generalized HSDD as characterized by low sexual desire that causes marked distress or interpersonal difficulty and is not due to a co-existing medical or psychiatric condition, problems with the relationship, or the effects of a medication or drug substance.

In each of the above embodiments, the female patient may be premenopausal.

In each of the above embodiments, female patient may be premenopausal and the FSD is acquired, generalized HSDD as characterized by low sexual desire that causes marked distress or interpersonal difficulty and is not due to a co-existing medical or psychiatric condition, problems with the relationship, or the effects of a medication or drug substance.

In each of the above embodiments, the female patient may be postmenopausal.

In each of the above embodiments, female patient may be postmenopausal and the FSD is acquired, generalized HSDD as characterized by low sexual desire that causes marked distress or interpersonal difficulty and is not due to a co-existing medical or psychiatric condition, problems with the relationship, or the effects of a medication or drug substance.

EXAMPLES

The following examples are used for illustrative purposes only, and are not to be construed as limiting.

Example 1

Review of information in IND 64119 by the Division of Bone, Reproductive, and Urologic Products (DBRUP) and the Division of Cardiovascular and Renal Products (DCRP) identified increases in systolic and diastolic blood pressures (BPs) with repeat doses of BMT (approximately 4 mmHg, with effect lasting at least four hours). Given the relationship between elevations in BP and adverse cardiovascular (CV) outcomes, there was concern that BMT use may increase the risk of CV events in women. As a result, the FDA required additional blood pressure studies. (Division of Bone, Reproductive, and Urologic Products Clinical Review, NDA 210557 SD 37 11/20/18)

Figure 1:
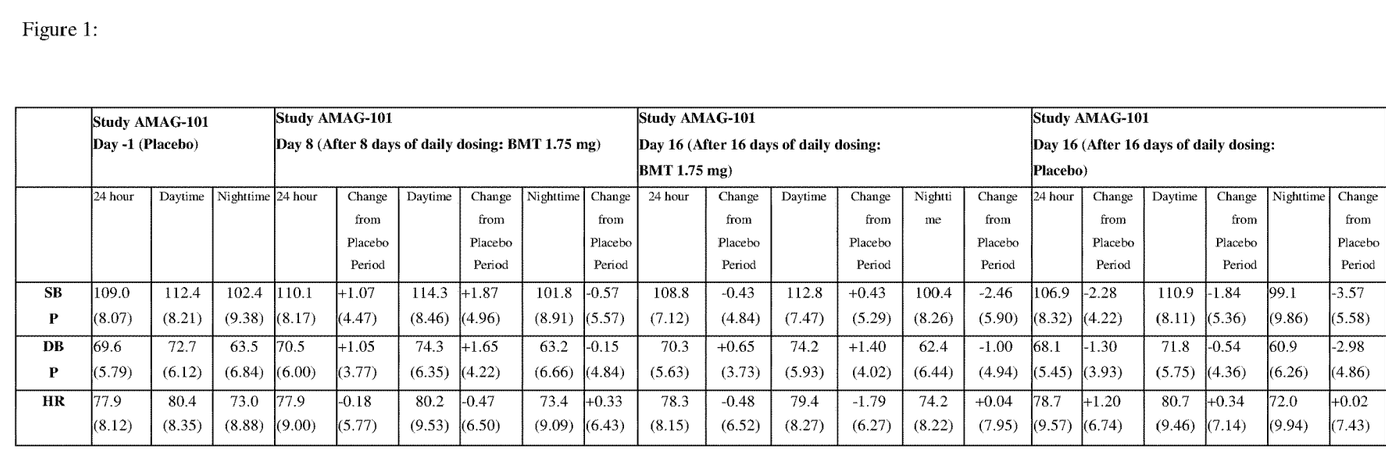
FIG. 1 depicts a table displaying the data from the repeated dosing trial of bremelanotide.

The study focusing on the impact of repeat dosing on blood pressure included 127 women treated with bremelanotide 1.75 mg administered subcutaneously (SC) daily for 8 consecutive days, followed by a randomized withdrawal period of 8 additional consecutive days (days 9 to 16) in which study participants were randomized to either remain on bremelanotide 1.75 mg SC daily or placebo SC daily. Ambulatory blood pressure monitoring was performed on baseline day −1 (single blind placebo), day 8 and on day 16. After 8 days of dosing of bremelanotide 1.75 mg SC, the mean changes from baseline in the 24 hour systolic and diastolic BPs (FIG. 1) were below 2 mmHg. Importantly, the upper bound of the 95% confidence interval for the mean changes in daytime systolic BP (a pre-specified outcome) was below 4 mmHg. These increases in BP were accompanied by small to no reductions in the heart rate of 1 beat/minute or less.

There were 122 (96%) study participants who completed the randomized withdrawal portion of the study. In the 61 women who received bremelanotide 1.75 mg SC for 16 consecutive days, changes from the placebo baseline period at Day −1 demonstrated increases in 24 hour BP of <1 mmHg and <1.5 mmHg for the average daytime BPs. In those randomized to placebo, returns toward baseline BP values were observed (generally a 2 mmHg decline from day 8). Outlier analyses from the study also demonstrated that 1 (0.8%) of the study participants had a systolic BP elevation of >150 mmHg or diastolic BP elevation >95 mmHg lasting for 120 minutes, and 2 (1.6%) had either a systolic BP elevation of >160 mmHg or a diastolic BP elevation of >100 mmHg that lasted for more than 90 minutes. These findings were comparable to the outlier numbers observed during the single-blind placebo treatment period (day −1). In none of these subjects were there complications or symptoms associated with the transient stage 2 hypertension levels.

The patient population was comprised of normotensive premenopausal women and included 2 women with a medical history of hypertension on antihypertensive therapy. One 38 yr old subject was being treated for hypertension with Lisinopril. The other 54 yr old subject was being treated for hypertension with chlorthalidone. Both subjects received all 16 injections; 8 doses in the Open-Label Period and 8 doses in the Randomized Withdrawal Period (one subject was randomized to each treatment group). Both subjects experienced at least one TEAE during the study; all were mild in intensity and considered related to study drug by the Investigator. No cardiovascular TEAE were reported and neither subject had clinically significant abnormalities on ECG. The mean changes from Baseline (Day −1) at Day 8 during daytime in these two subjects are shown in the below table. Changes in daytime HR at Day 8 were −1.7 bpm for the 38 yr old subject and −1.4 bpm for the 54 yr old subject. Importantly, the study drug did not significantly increase the blood pressure of these two women with a medical history of hypertension and who are on anti-hypertensive therapy.

| Subject Age | Baseline (Day-1) Daytime BP | Day 8 Daytime BP | Difference from Baseline |
|---|---|---|---|
| 38 | 105/70 mmHg | 108/74 mmHg | +3 systolic; +4 diastolic |
| 54 | 121/81 mmHg | 112/77 mmHg | −9 systolic; −4 diastolic |

In order to better understand the potential effects of the drug in patients with higher BP values at baseline, an exploratory analysis was performed from the trial evaluating those women whose baseline BP was in the 90$^{th}$ percentile (pre-dose systolic BP >124 mmHg) to determine if the pressor response of bremelanotide differed from those study participants whose baseline BP was below the 90th percentile (pre-dose systolic BP <124 mmHg). At day 8, mean changes (95% CI) from the daytime systolic BP in those study participants in the 90$^{th}$ percentile or greater (n=17) at baseline was −0.16 (−2.06, 1.75) mmHg versus 2.03 (1.70, 2.36) mmHg in those whose baseline systolic BP was below the 90$^{th}$ percentile. Trends were similar after 16 days of dosing of bremelanotide 1.75 g SC. These data demonstrate no excess increase in BP on bremelanotide in premenopausal women who had higher baseline BPs.

In conclusion, the phase 1 study in 127 healthy premenopausal women evaluating multiple consecutive day doses of bremelanotide, 1.75 mg SC demonstrated that:

Following 8 consecutive days of dosing of bremelanotide, small (<2 mmHg) increases in 24 hour systolic BP were observed in association with peak effects 3-5 hours post-dose that attenuated by 8 hours post-dose. The upper bound of the 95% confidence interval for changes in daytime systolic BP (primary outcome) was <4 mmHg (2.7 mmHg). There were no increases in nighttime BP observed following 8 days of consecutive therapy.

In those study participants randomized to remain on bremelanotide for a total of 16 days of consecutive administration, no cumulative increases in daytime BP or reductions in heart rate compared to baseline or to day 8 of the study were observed.

In those study participants randomized to be withdrawn from bremelanotide and administered placebo from days 9 to 16 of the study, small reductions (2 mmHg) in daytime systolic BP were seen following day 8 and resultant BPs were similar to those at baseline before drug administration (day −1).

The study provided no evidence that women with higher baseline BP values have larger excursions in ambulatory BP than women with lower baseline BP values after 8 and 16 consecutive days of bremelanotide administration.

Following consecutive daily doses of bremelanotide for up to 16 days, the magnitude of the pressor effect of bremelanotide remained small confirming no cumulative effect of repeated administration of the drug. Based on the results of the placebo withdrawal period, the small increases in BP observed with bremelanotide were found to be transient and reversible.

Example 2

An additional study evaluated the effects of single doses of bremelanotide 1.75 mg SC and placebo SC in normotensive, healthy women pre-treated with 5 different classes of antihypertensive drugs in a double-blind cross-over design using ambulatory BP monitoring. The washout period between randomized, blinded treatments was 48 hours. This study included both premenopausal and postmenopausal women. There were 15 healthy premenopausal subjects in each panel of the antihypertensive medications with the exception of the beta-blocker metoprolol (n=17). Blood pressures at baseline in the various panels were low normal (24 hour systolic BPs ranging from 109 to 114 mmHg and 24 hour diastolic BPs ranging from 67 to 72 mmHg (FIG. 2). The placebo-corrected changes from baseline in the 24-hour systolic BPs on bremelanotide 1.75 mg SC ranged from 1.7 mmHg on amlodipine to 3.8 mmHg on hydrochlorothiazide; changes in the 24 hour diastolic BPs ranged from 1.8 mmHg on metoprolol to 2.8 mmHg on lisinopril. In 4 of the 5 classes of antihypertensive medications, nighttime BP changes were substantially lower than daytime BP changes. In study participants pre-treated with hydrochlorothiazide 12.5 mg daily, nighttime BPs increased by 5.5/4.5 mmHg. In review of individual subjects in the HCTZ panel, it was noted that 4 study participants had large reductions in nighttime SBP (10-15 mmHg) on placebo while on bremelanotide 4 study participants had large increases in nighttime SBP (10-15 mmHg). These findings do not have a pharmacologic basis; thus, the mean difference in nocturnal BP on bremelanotide relative to placebo in this subgroup likely occurred on a random basis.

| Time Post-Dose | Bremelanotide 2 mg SC (n = 30) | Placebo (n = 27) |
|---|---|---|
| Systolic Blood Pressure | | |
| Hour 1 | 2.36 (−2.15, 6.87) | −1.90 (−6.31, 2.50) |
| Hour 2 | 0.01 (−4.18, 4.20) | −0.58 (−3.83, 2.67) |
| Hour 3 | 0.84 (−3.55, 5.23) | −1.25 (−4.29, 1.78) |
| Hour 4 | 0.38 (−3.13, 3.90) | −0.43 (−4.11, 3.25) |
| Diastolic Blood Pressure | | |
| Hour 1 | 1.00 (−3.13, 5.13) | −4.05 (−8.07, −0.03) |
| Hour 2 | 1.03 (−2.96, 5.02) | −0.31 (−3.51, 2.89) |
| Hour 3 | 1.26 (−2.74, 5.26) | −0.45 (−3.09, 3.98) |
| Hour 4 | −1.38 (−6.00, 3.24) | 1.69 (−1.34, 4.73) |

In conclusion, based on data from these supportive studies:

1. The drug-drug interaction study with antihypertensive agents in 77 pre-and postmenopausal women (n=15 to 17 per antihypertensive panel) demonstrated that a single dose of bremelanotide 1.75 mg SC induced small, consistent increases in 24 hour systolic BP which attenuated during the 2$^{nd}$ half of the dosing interval for 4 of the 5 classes studied. Of note, the baseline BPs in these healthy women treated with antihypertensive therapy at steady-state were low normal; therefore, the increases in BP observed did not induce hypertension in the study participants. There was an elevation in nighttime BP in patients pre-treated with hydrochlorothiazide 12.5 mg, which has no apparent pharmacologic basis and is like the result of random variability in both the bremelanotide and placebo sub-groups. As noted, there was no similar finding in the 4 other antihypertensive panels.

2. The magnitude of pressor effect of bremelanotide in obese women receiving supratherapeutic doses (6.5 mg daily) was similar to that observed in the studies utilizing 1.75 mg daily. During 15 days of bremelanotide at this high daily dose, there was no evidence for a cumulative effect on blood pressure or heart rate.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above are hereby incorporated by reference.

What is claimed is:

1. A method for treating female sexual dysfunction in a female patient diagnosed with female sexual dysfunction, said method comprising administering more than a single subcutaneous injection of a composition comprising bremelanotide or a pharmaceutically acceptable salt of bremelanotide to the female patient when the patient is anticipating sexual activity, wherein the female patient has controlled hypertension, wherein the composition comprises 1.25 mg to 1.75 mg net peptide weight of bremelanotide, and wherein there is at least 24 hours between each injection and no more than eight injections are administered in a month, thereby treating female sexual dysfunction.

2. A method for treating female sexual dysfunction in a female patient diagnosed with female sexual dysfunction, said method comprising administering more than a single subcutaneous injection of a composition comprising bremelanotide or a pharmaceutically acceptable salt of bremelanotide to the female patient when the patient is anticipating sexual activity, the composition comprising 1.25 mg to 1.75 mg net peptide weight of bremelanotide sufficient to result in a peak plasma concentration of bremelanotide of no more than 120 ng/mL within 60 minutes after administration of the composition, wherein the female patient also has controlled hypertension, and wherein there is at least 24 hours between each injection and no more than eight injections are administered in a month, thereby treating female sexual dysfunction.

3. A method for treating female sexual dysfunction in a female patient diagnosed with female sexual dysfunction, said method comprising administering more than a single subcutaneous injection of a composition comprising bremelanotide or a pharmaceutically acceptable salt of bremelanotide to the female patient when the patient is anticipating sexual activity, the composition comprising an amount of bremelanotide sufficient to result in a peak plasma concentration of bremelanotide of no more than 120 ng/ml within 60 minutes after administration of the composition, wherein the composition comprises 1.50 mg to 1.75 mg net peptide weight of bremelanotide, wherein the female patient also has controlled hypertension, and wherein there is at least 24 hours between each injection and no more than eight injections are administered in a month, thereby treating female sexual dysfunction.

4. The method of claim 3, wherein the peak plasma concentration of bremelanotide is no more than 100 ng/mL within 60 minutes after administration of the composition.

5. The method of claim 3, wherein the composition is an aqueous solution comprising an acetate salt of bremelanotide.

6. The method of claim 5, wherein the acetate salt of bremelanotide is between 6% and 12% acetic acid (w/w) in an aqueous solution of bremelanotide.

7. The method of claim 6, wherein the composition has a pH of 5.0, and wherein the composition further comprises one or more agents to adjust pH.

8. The method of claim 7, wherein the one or more agents to adjust pH are selected from the group consisting of hydrochloric acid and sodium hydroxide.

9. The method of claim 3, wherein the variability in peak plasma concentration within 60 minutes after subcutaneous administration of the composition is a percent coefficient of variation (% CV) less than 30.

10. The method of claim 3, wherein the female sexual dysfunction is decreased sexual desire.

11. The method of claim 3, wherein the female sexual dysfunction is hypoactive sexual desire disorder.

12. The method of claim 3, wherein the female sexual dysfunction is hypoactive sexual desire disorder with female sexual arousal disorder.

13. The method of claim 3, wherein the female sexual dysfunction is hypoactive sexual desire disorder without female sexual arousal disorder.

14. The method of claim 3, wherein the composition is an aqueous solution comprising an acetate salt of bremelanotide and glycerin.

15. The method of claim 14, wherein the composition comprises 2.5% glycerin (w/v).

16. The method of claim 3, wherein the patient is concurrently taking no more than two anti-hypertensive drugs.

17. The method of claim 3, wherein the patient has consistently maintained their systolic blood pressure below 130 mm Hg.

18. The method of claim 3, wherein the patient has consistently maintained their diastolic blood pressure below 80 mm Hg.

19. The method of claim 3, wherein the composition is provided in a single-use pre-filled syringe.

* * * * *